(12) United States Patent
Packman et al.

(10) Patent No.: US 6,228,035 B1
(45) Date of Patent: May 8, 2001

(54) UNIVERSAL CUFF FOR A BLOOD PRESSURE MONITOR (75) Inventors: Jay D. Packman, Edgewater; John B. Wilson, Wanaque, both of NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/343,346

(22) Filed: Jun. 30, 1999

(51) Int. Cl.[7] .................................................. A61B 5/02

(52) U.S. Cl. .......................... 600/485; 600/490; 128/900

(58) Field of Search ................................... 600/300, 301, 600/481, 485–499; 128/900

(56) References Cited

U.S. PATENT DOCUMENTS

| 4,493,326 | * | 1/1985 | Hill et al. ............................. 600/300 |
| 5,172,697 | * | 12/1992 | Koven et al. ......................... 600/300 |

* cited by examiner

Primary Examiner—Cary O'Connor
Assistant Examiner—Michael Astorino
(74) Attorney, Agent, or Firm—Alan W. Fielder, Esq.

(57) ABSTRACT

A universal cuff for a blood pressure monitor that has a usable length that is variable so that it can be used on a wide range of arm circumferences. The universal cuff includes a mechanism for setting the usable length having a shutoff cam and a D-ring. A blood pressure monitor is also presented having a mechanism for determining the usable length of the cuff by measuring inflation rate or by controlling a deflation rate control valve during deflation.

18 Claims, 9 Drawing Sheets

FIG-1 PRIOR ART

FIG-2 BLOOD PRESSURE MONITOR WITH AUTOMATIC CUFF SIZE DETECTION

UNIVERSAL CUFF FOR A BLOOD PRESSURE MONITOR

BACKGROUND OF THE INVENTION

1. Field of the Invention

The present invention relates to a universal blood pressure cuff for an automated blood pressure monitor system.

2. Description of Related Art

Arterial blood pressure has been found to be an important indicator of a person's health and its measurement has become a part of every complete physical examination. Blood pressure monitoring is used to screen patients for hypertension and other illnesses. In particular, an inappropriate low pressure may signify a medical emergency while an inappropriate high blood pressure is a marker for hypertension which has been found to be a major risk factor for premature cardiovascular and other vascular diseases. In addition, diabetics have now been encouraged to regularly monitor their blood pressure in order to reduce medical complications caused by diabetes.

Therefore, the requirement for the use of blood pressure monitors in the home has increased substantially and therefore the need for improved and intuitive blood pressure monitors has become even more necessary.

Figure 1:
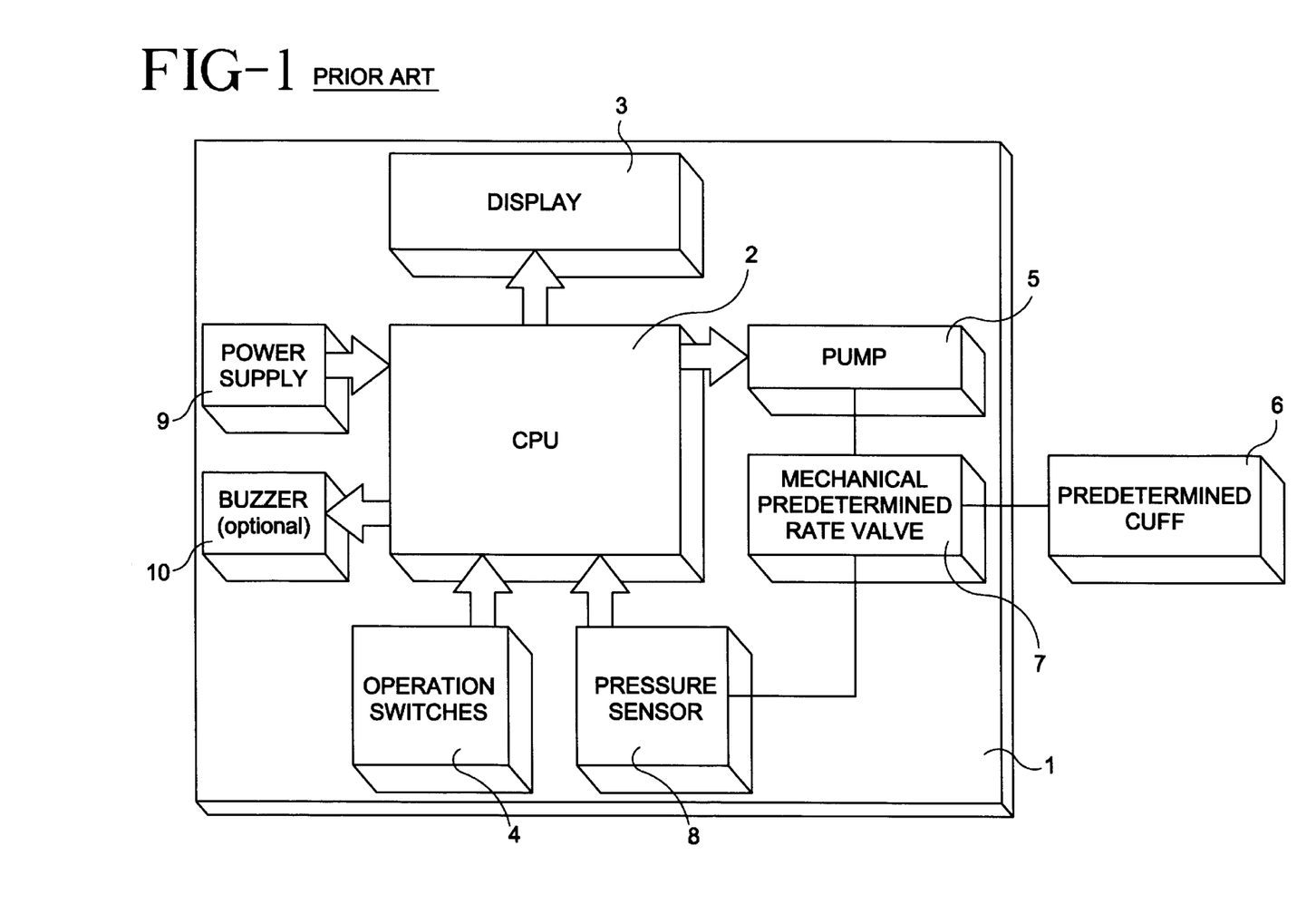
FIG. 1 is a block diagram of a conventional blood pressure monitor.

FIG. 1 is a block diagram of a conventional blood pressure monitor 1 including a CPU 2 for controlling blood pressure monitor 1, a display 3 for displaying status information and the blood pressure measured by blood pressure monitor 1, operation switches 4 for activating and otherwise controlling blood pressure monitor 1, a pump 5 connected to a cuff 6 having predetermined dimensions through a predetermined deflation rate valve 7. Blood pressure monitor 1 also includes a pressure sensor 8 that measures the pressure within cuff 6 and provides that information to CPU 2 for display on display 3. Blood pressure monitor 1 also includes a power supply 9 and an optional buzzer 10, which provides audible signaling to the user as needed by blood pressure monitor 1.

Cuff 6 in the conventional blood pressure monitor 1 is specifically designed for use only with blood pressure monitor 1 and has predetermined dimensions including width, length, volume, etc. Historically, cuff size has been a very controversial subject and has caused the need for guidelines that are recommended in regards to the relationship between the patient's arm circumference to bladder coverage and the geometry of the bladder itself in order for the blood pressure monitor 1 to obtain a correct reading. A requirement to have a predetermined cuff 6 has created issues of being able to have one blood pressure monitor that will allow the use of almost any size cuff without having to do a manual adjustment each time. Manual adjustment would be required due to the fact that conventional blood pressure monitors require not only a constant deflation rate but a deflation rate that is within a specific range, typically, three to six mmHg/sec. For example, when a blood pressure monitor is set for predetermined cuff 6 and a larger cuff is used, the deflation rate would be so slow that it would be very uncomfortable to the patient. In addition, if a smaller cuff than predetermined cuff 6 is used, the deflation rate would be increased causing inaccurate results.

It is also known that there is significant range of arm circumferences across the population of patients resulting in the need for different size cuffs for different arm circumferences that are still required to fit within the recommended guidelines. For example, conventional blood pressure monitors have a cuff 6 with a circumference range of 20 cm to 30 cm. If the arm circumference is 25 cm, then the pressure reading might be right, but if the arm circumference is 30 cm, blood pressure monitor 1 may produce an acceptable error due to "undercuffing". In addition, if the arm circumference is 20 cm blood pressure monitor 1 would produce an acceptable error due to "overcuffing". These measurements may still be accurate but would not be precise. To use blood pressure monitor 1 outside the above range would require the use of different size predetermined cuffs 6, smaller cuffs for smaller arm circumferences and larger cuffs for larger arm circumferences. To provide such an assortment of arm circumference sized cuffs is a burden to the healthcare worker and adds additional costs to the blood pressure monitor.

Hence, it is necessary to provide a universal blood pressure cuff that can be used on a range of arm circumferences that represent the typical population of patients.

SUMMARY OF THE INVENTION

The present invention relates to a universal blood pressure cuff for use on a new blood pressure monitor that addresses the above-identified problems. In addition, the blood pressure monitor of the present invention will eliminate the need for the user or healthcare professional to only use a predetermined cuff size. The present invention provides a one size fits all cuff that has better precision since the blood pressure monitor accounts for a variation in arm circumference and prevents the consumer from using the wrong sized cuff for their measurement.

The present invention determines cuff size by analyzing the inflation rate of the cuff or the deflation characteristics of the cuff and uses this information to determine the pressure adjustment needed to display accurate blood pressure readings.

These and other aspects, features and advantages of the present invention, will become apparent from the following detailed description taken in conjunction with the accompanying drawings.

DETAILED DESCRIPTION

Figure 2:
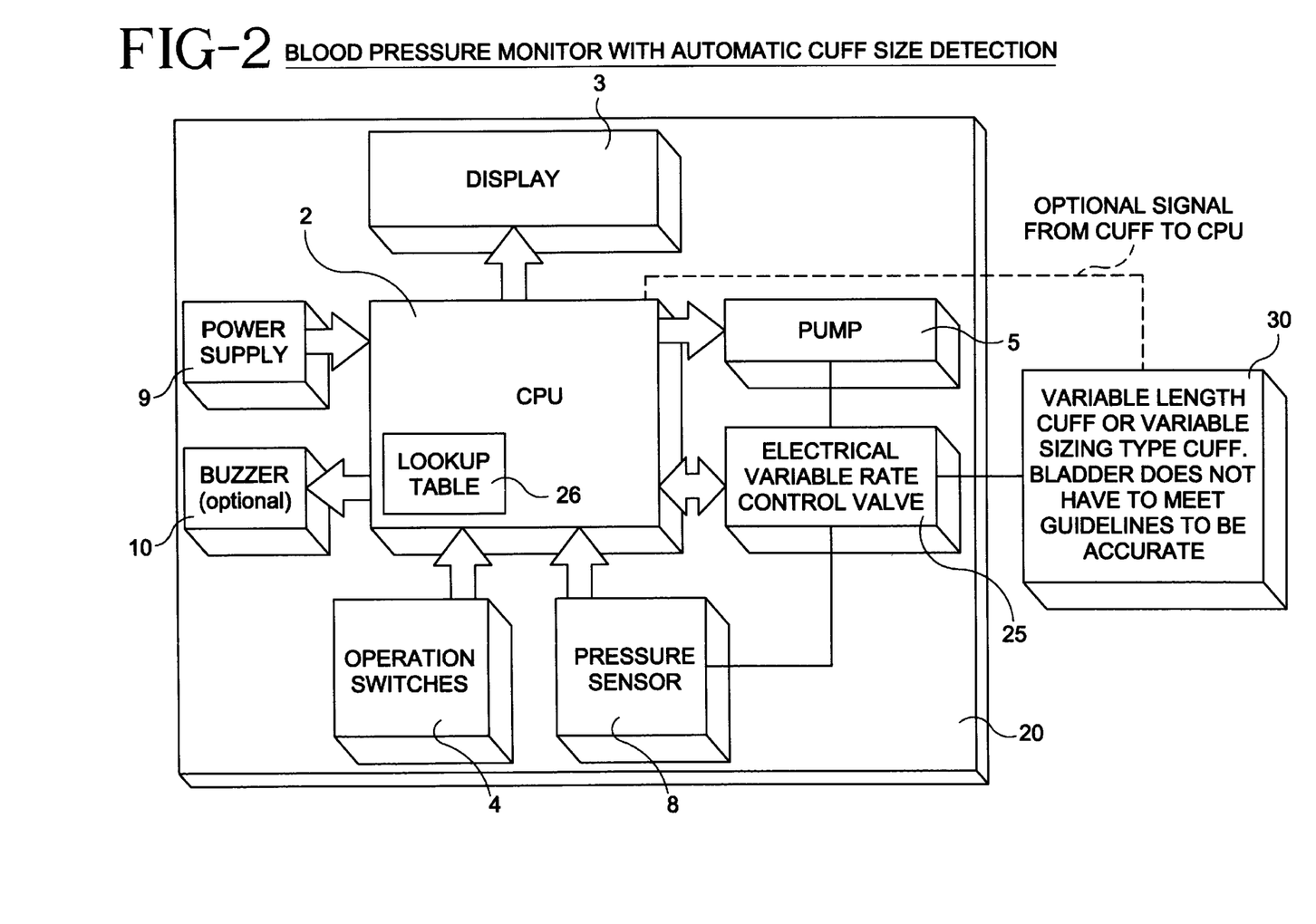
FIG. 2 is a block diagram of a blood pressure monitor according to the present invention.

A blood pressure monitor 20 according to the present invention is shown as a block diagram in FIG. 2. All of the elements that are common to the conventional blood pressure monitor 1 shown in FIG. 1 have the same reference numerals. In particular, CPU 2, display 3, operation switches 4, pump 5, pressure sensor 8, power supply 9, and optional buzzer 10. Blood pressure monitor 20 includes an electrical variable deflation rate control valve 25 and a universal variable length cuff 30 according to the present invention. Universal cuff 30 is a cuff having a variable length or variable sizing with a bladder that is not required to meet the guidelines conventionally used to provide accurate blood pressure readings.

Figure 3A:
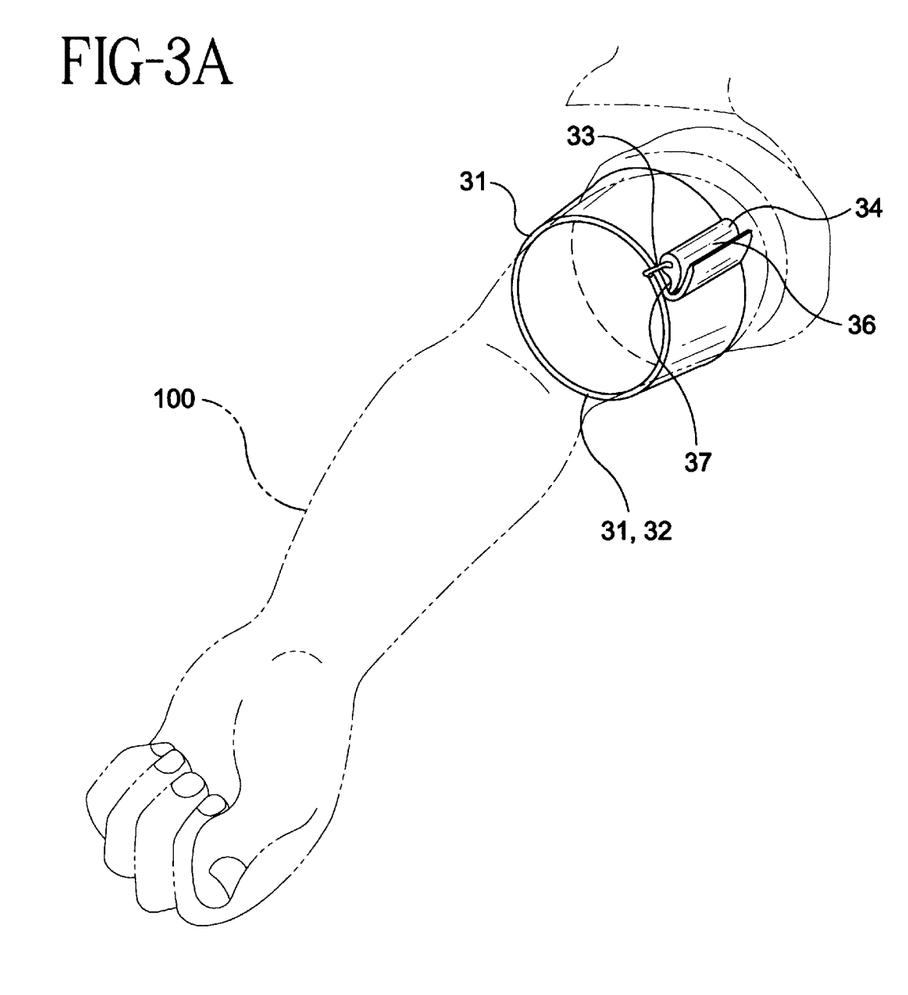
FIGS. 3A and 3B are perspective views of a cuff according to the present invention as shown in FIG. 2.
Figure 3B:
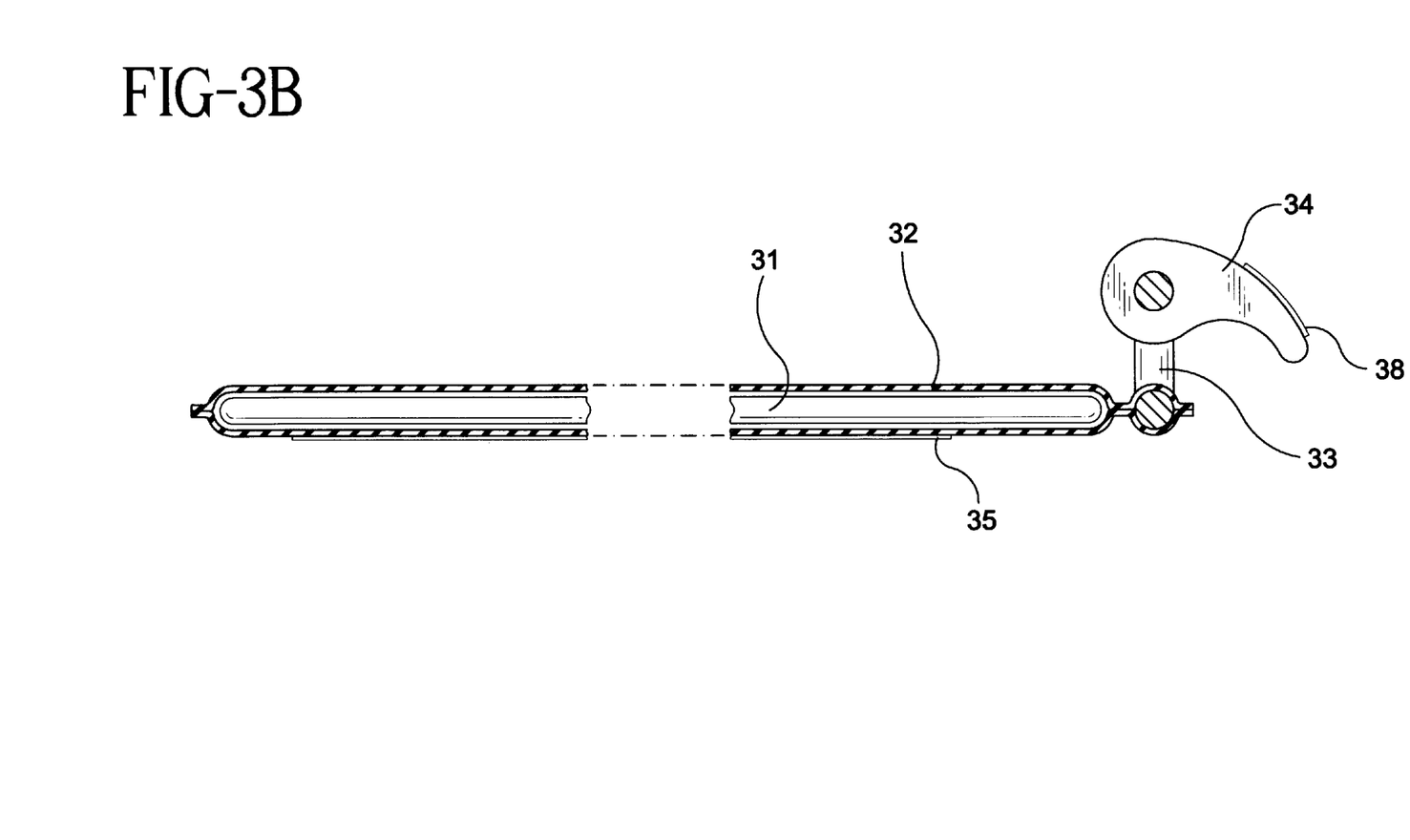

FIG. 3A is a perspective view of universal cuff 30 wrapped on a patient's arm 40 and shows a bladder 31, an outer shell 32 (as shown in FIG. 3B) and a mechanism 33–37 for holding cuff 30 on arm 40. Mechanism 33–37, as shown in FIG. 3A, includes a D-ring 33 attached to one end of cuff 30 with the other end of cuff 30 extending through D-ring 33 and being attached to shut off cam 34 by hook and fasteners 35 and 36. Shut off cam 34 has an inner surface 37 that together with D-ring 33 seals and closes off bladder 31 within cuff 30 to set the length of bladder 31 to the circumference of arm 40. FIG. 3A also shows that cuff 30 has a width W which is known over the entire length of cuff 30. Therefore, the only dimension that varies during the use of cuff 30 between different size arms 40 is the length of the usable portion of bladder 31.

Electrical variable deflation rate control valve 25, shown in FIG. 2, is used to control the deflation rate and set the deflation rate to a desired constant value. Valve 25, therefore, permits blood pressure monitor 20 to be used with any length bladder 31.

Figure 4:
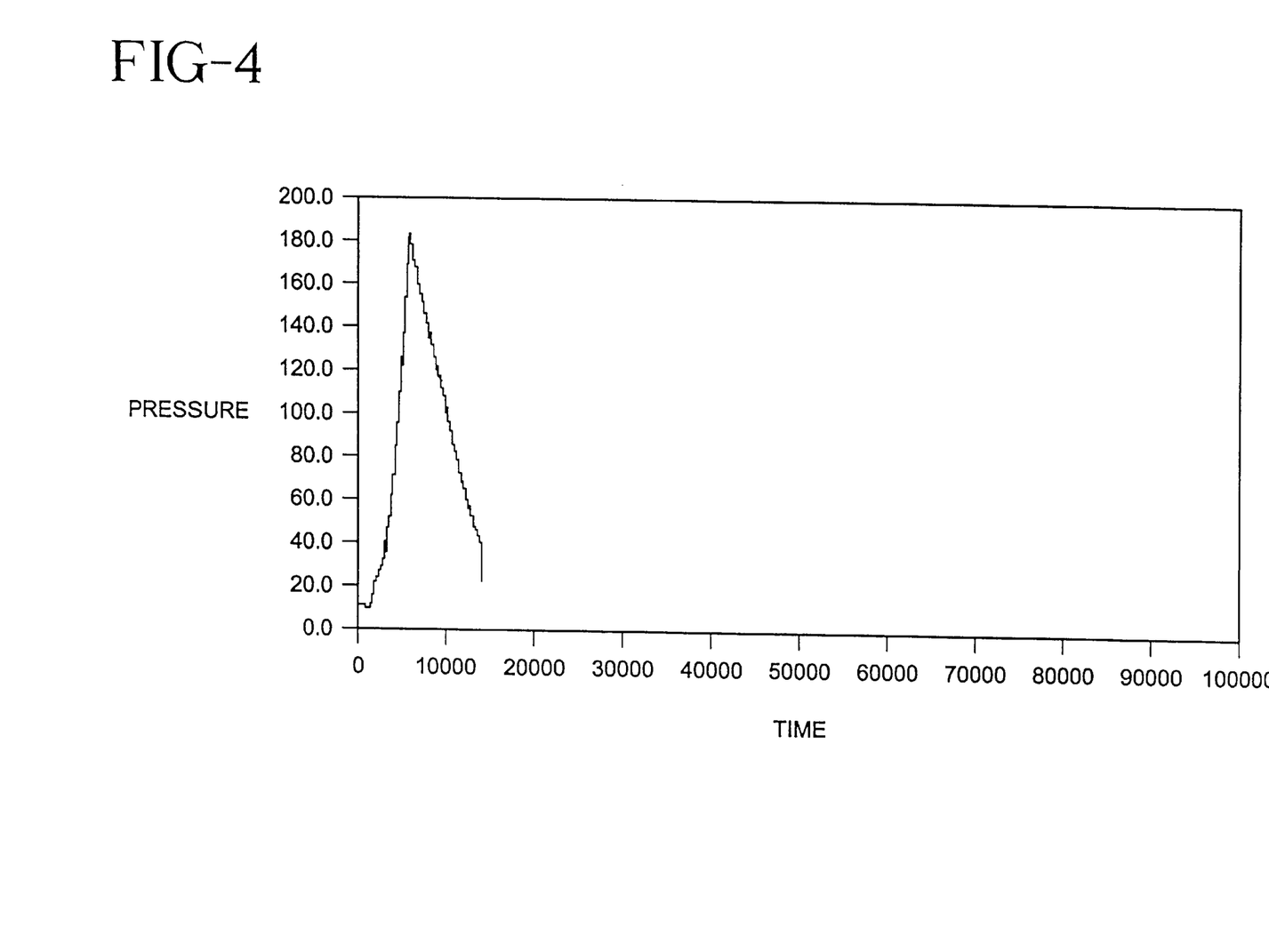
FIG. 4 is a plot of pressure versus time for predetermined cuff 6 having a small bladder used with conventional blood pressure monitor 1, shown in FIG. 1.
Figure 5:
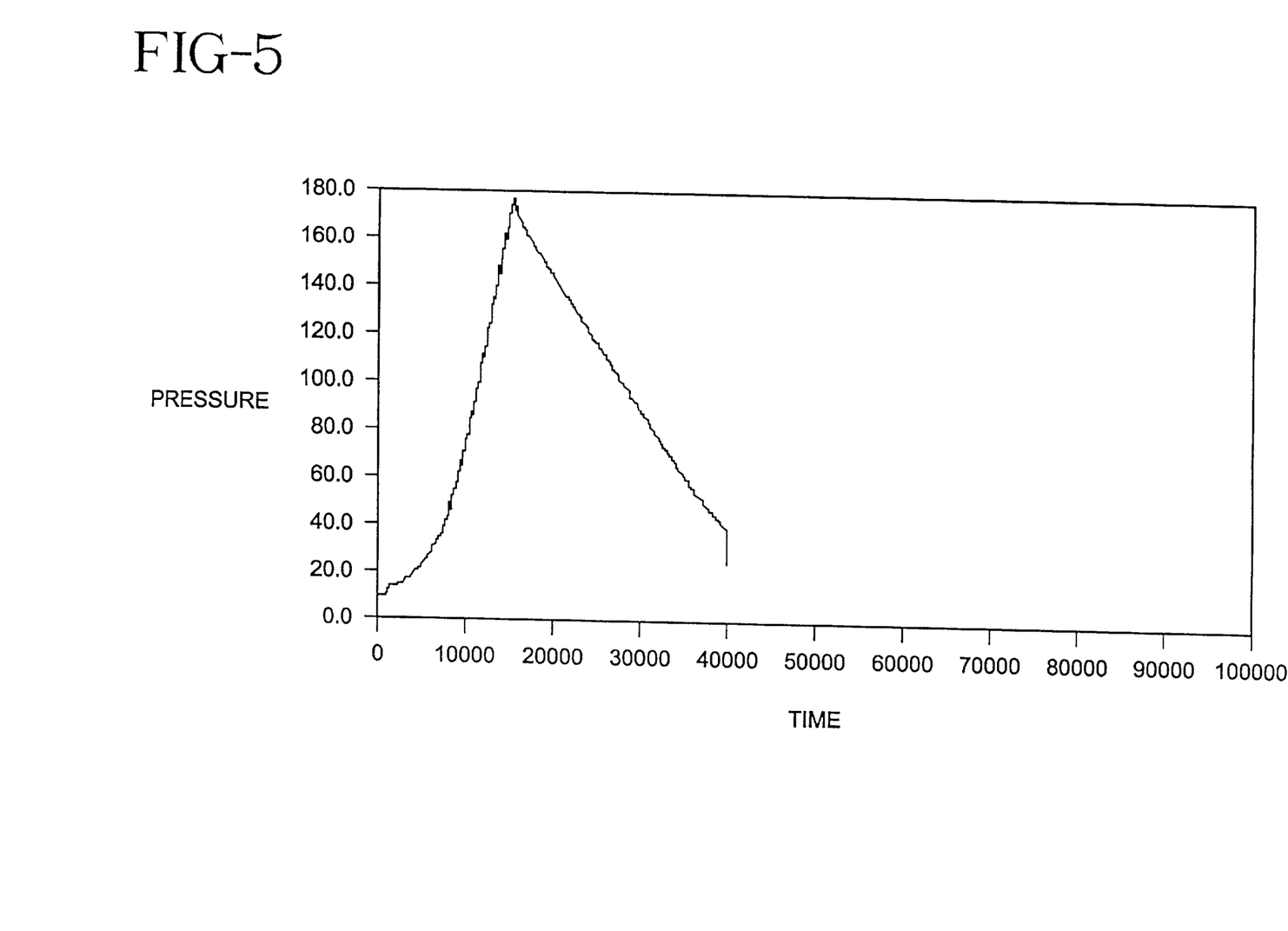
FIG. 5 is a plot of pressure versus time for predetermined cuff 6 having a medium bladder used with conventional blood pressure monitor 1, shown in FIG. 1.
Figure 6:
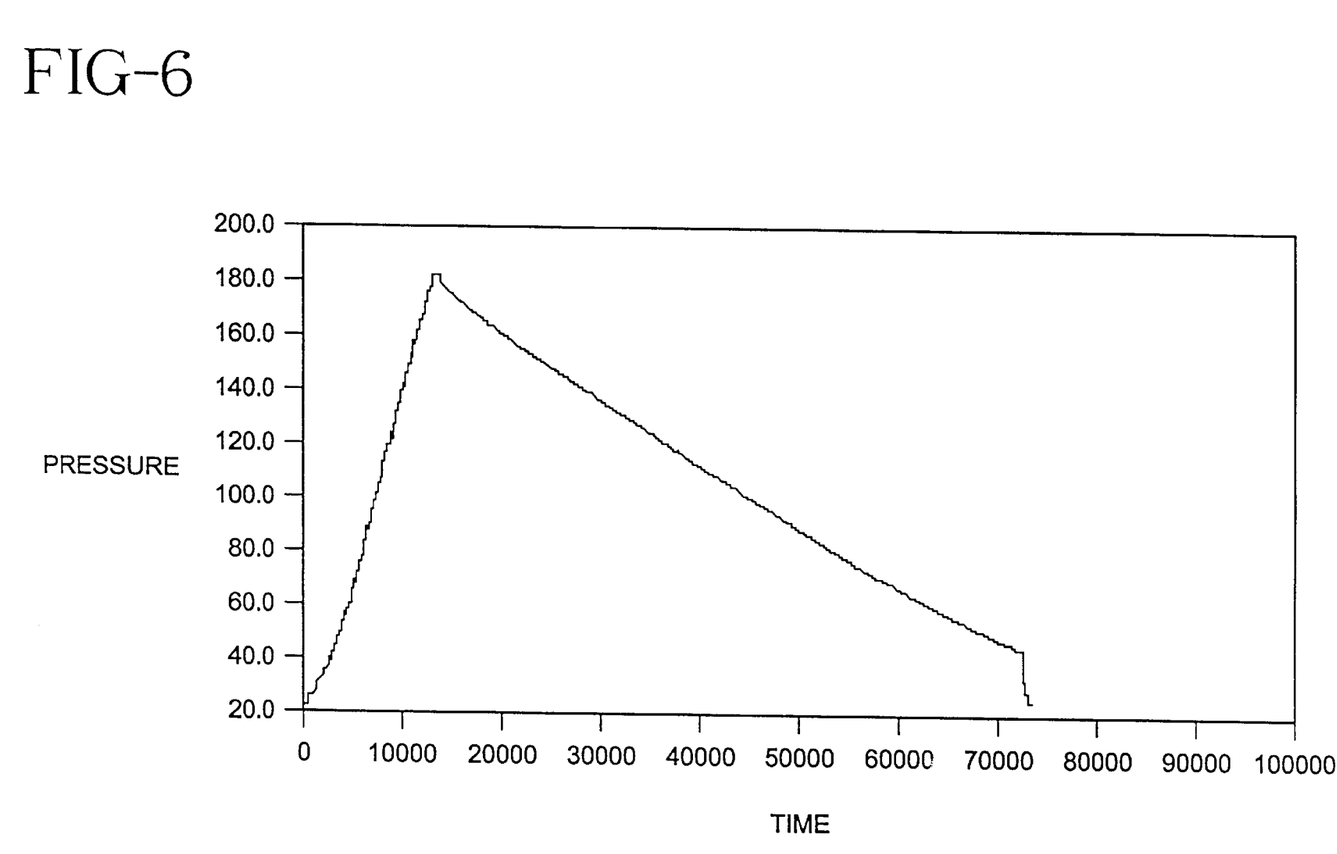
FIG. 6 is a plot of pressure versus time for predetermined cuff 6 having a large bladder used with conventional blood pressure monitor 1, shown in FIG. 1.

FIGS. 4–6 are plots of pressure versus time for predetermined cuff 6, shown in FIG. 1, having small, medium, and large length bladders, respectively. These plots show that when keeping valve 7, in FIG. 1, at a constant setting and changing the length and therefore volume of the bladder, the deflation rate changes in a manner that is predictable. As shown in FIGS. 4–6, the deflation rate of a bladder decreases as the bladder volume increases. For example, FIG. 4 shows a deflation rate of –11.76 for the small bladder, FIG. 5 shows a deflation rate of –4.3 for the medium bladder, and FIG. 6 shows a deflation rate of –2.68 for the large bladder. To ensure accuracy and comfort, it is necessary for the deflation rate to be set to a predetermined value typically within the range of 3 to 6 ml of mercury per second. Since valve 25 of the present invention is electrically variable, CPU 2 can determine how open or closed valve 25 needs to be in order to provide the necessary constant deflation rate within that range. Based on the setting of valve 25, CPU 2 can determine the length of bladder 31 used for arm 40 in FIG. 3A.

The present invention allows cuff 30 to be designed to meet 80 to 100% circumference coverage for a very wide range of arm circumferences, many of which would typically violate the guidelines.

Figure 7:
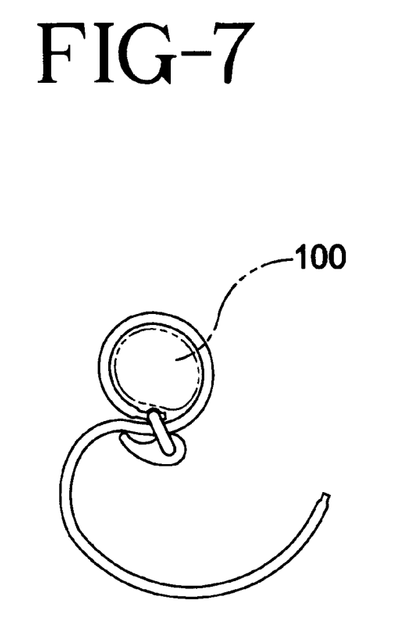
FIG. 7 is a cross sectional view of the cuff of the present invention on a small arm.
Figure 8:
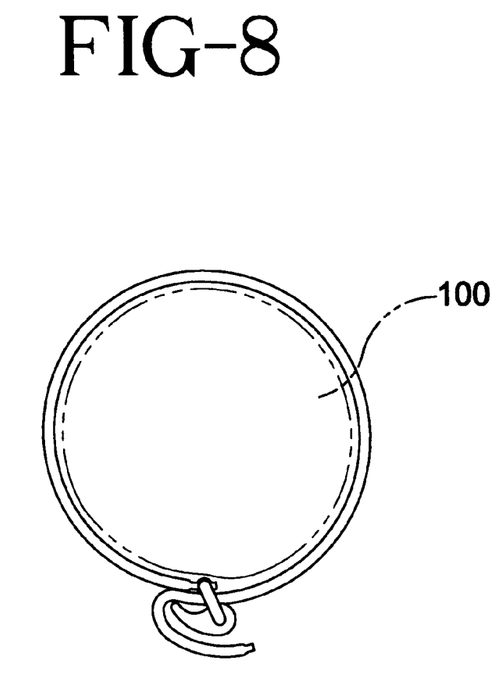
FIG. 8 is a cross sectional view cuff of the present invention on a large arm.
Figure 9:
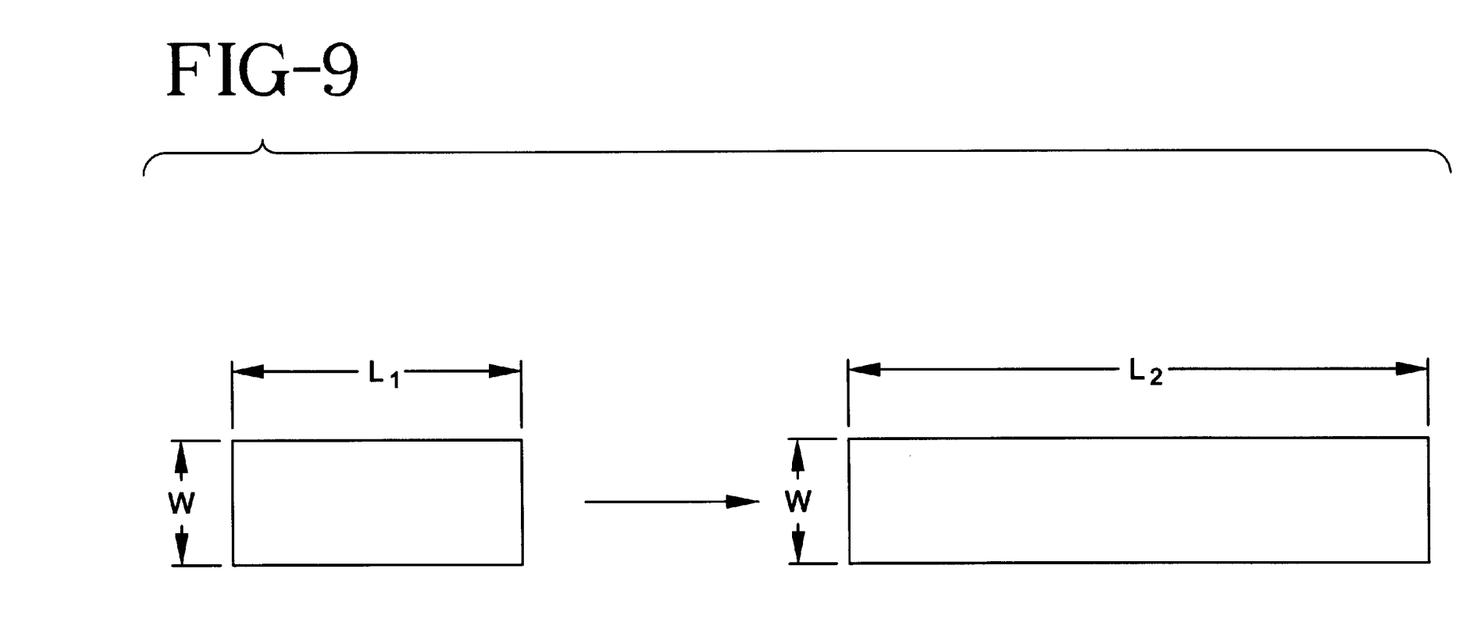
FIG. 9 shows the relationship between the bladder size of the cuff shown in FIG. 7 versus the cuff shown in FIG. 8.

FIGS. 7 and 8 show the use of cuff 30 on a small arm and a large arm, respectively, and FIG. 9 shows how the width W of bladder 31 is known between both uses but the length of bladder 31 being used in each use varies from $L_1$ in FIG. 7 to $L_2$ in FIG. 8. Therefore, the volume of bladder 31 between FIG. 7 and FIG. 8 also increases from $V_1=L_1\times W$ to $V_2=L_2\times W$. This change in volume and length is determined, as described above, by the position of valve 25. In addition, an optional signal directly from cuff 30 can be provided to CPU 2 that directly indicates the arm circumference and therefore the length of bladder 31 being used and therefore the volume so that CPU 2 can perform the blood pressure monitoring process. The signal from cuff 30 could be based upon the amount of bladder used and could be considered a smart cuff type system.

After valve 25 has been set to the constant deflation rate, CPU 2 uses pressure sensor 8 to measure the pressure in bladder 31 through valve 25 and provide the pressure measurement to CPU 2. CPU 2 then translates the pressure measurement from pressure sensor 8 into blood pressure readings using the oscillometric technique or the auscultation technique, commonly used by conventional electronic blood pressure monitors. The oscillometric method is based on detecting the oscillations on the lateral walls of the occluded artery as the cuff is deflated. These techniques are known to be accurate if cuffs within the guidelines are used. However, the present invention uses a new cuff 30 having a variable volume and length and therefore not necessarily within the guidelines. To properly adjust the blood pressure reading determined by the oscillometric technique to account for the deviation from the guidelines, CPU 2 adjusts the readings using a predetermined lookup table 26 that correlates the used length of bladder by a necessary offset to bring the blood pressure readings within the guidelines.

Alternatively, the length of the used bladder 31 can be determined during the inflation process by monitoring the inflation rate using pressure sensor 8 over time, since the inflation rate varies depending on size of the bladder when pump 5 is kept at a constant rate. For example, as shown in FIGS. 4–6 the inflation rate is faster for a small bladder and slower for a large bladder. After the size of the bladder has been determined, valve 25 is set to provide a desired deflation rate for that particular size bladder. The remainder of the process is the same as described above.

While the present invention has been described with respect to a preferred embodiment and an alternative embodiment, it is apparent that various changes can be made to these embodiments without departing from the scope of the invention as defined by the intended claims. For example, a variable pump 5 can be used to fill cuff 30 to a predetermined pressure measured by pressure sensor 8. Pump 5 would quickly inflate pump 30 to a first predetermined pressure and then slow the rate of fill until the predetermined final pressure has been obtained.

What is claimed is:

1. A blood pressure monitor for use with a blood pressure cuff having a variable usable length bladder, said blood pressure monitor comprising means for determining a usable length of said bladder.

2. The blood pressure monitor according to claim 1, wherein said means for determining said usable length of said bladder comprises:
   means for measuring the inflation rate of said bladder; and
   means for analyzing said measured inflation rate to determine said usable length.

3. The blood pressure monitor according to claim 1, further comprising:
   a deflation rate control valve for setting the deflation rate of said bladder; and
   means for measuring pressure within said bladder.

4. The blood pressure monitor according to claim 3, wherein said means for determining said usable length of said bladder comprises means for adjusting the deflation rate control valve based upon the pressure measured within said bladder to obtain a deflation rate between 3 to 6 mmHg/sec.

5. The blood pressure monitor according to claim 4, wherein said means for determining said usable length of said bladder further comprises means for analyzing the adjustments made by said adjusting means to determine said usable length of said bladder.

6. The blood pressure monitor according to claim 5, further comprising:

means for calculating a blood pressure; and means for adjusting the calculated blood pressure to a more accurate blood pressure based upon said measured usable length of said bladder.

7. The blood pressure monitor according to claim 6, wherein said means for adjusting the calculated blood pressure to the more accurate blood pressure based upon said measured usable length of said bladder is a lookup table.

8. The blood pressure monitor according to claim 6, wherein said means for calculating the blood pressure uses an oscillometric technique.

9. The blood pressure monitor according to claim 6, wherein said means for calculating the blood pressure uses an auscultation technique.

10. The blood pressure monitor according to claim 2, further comprising:

means for calculating a blood pressure; and means for adjusting the calculated blood pressure to a more accurate blood pressure based upon said measured usable length of said bladder.

11. The blood pressure monitor according to claim 10, wherein said means for adjusting the calculated blood pressure to the more accurate blood pressure based upon said measured usable length of said bladder is a lookup table.

12. The blood pressure monitor according to claim 10, wherein said means for calculating the blood pressure uses an oscillometric technique.

13. The blood pressure monitor according to claim 10, wherein said means for calculating the blood pressure uses an auscultation technique.

14. The blood pressure monitor according to claim 10, wherein said means for calculating the blood pressure calculates the blood pressure during inflation of said bladder.

15. The blood pressure monitor according to claim 1, wherein said means for determining said usable length of said bladder comprises:

means for measuring the deflation rate of said bladder; and means for analyzing said measured deflation rate to determine said usable length.

16. The blood pressure monitor according to claim 15, further comprising:

means for calculating a blood pressure; and means for adjusting the calculated blood pressure to a more accurate blood pressure based upon said measured usable length of said bladder.

17. The blood pressure monitor according to claim 16, wherein said means for adjusting the calculated blood pressure to the more accurate blood pressure based upon said measured usable length of said bladder is a lookup table.

18. The blood pressure monitor according to claim 16, wherein said means for calculating the blood pressure calculates the blood pressure during inflation of said bladder.

* * * * *